United States Patent [19]

Riegger

[11] 4,199,988
[45] Apr. 29, 1980

[54] SAMPLING APPARATUS FOR CHROMATOGRAPHIC INSTRUMENTS

[75] Inventor: Hubertus Riegger, Uberlingen, Fed. Rep. of Germany

[73] Assignee: Bodenseewerk Perkin-Elmer & Co., GmbH, Uberlingen, Fed. Rep. of Germany

[21] Appl. No.: 26,711

[22] Filed: Apr. 3, 1979

[30] Foreign Application Priority Data

Apr. 7, 1978 [DE] Fed. Rep. of Germany ....... 2815023

[51] Int. Cl.² ............................................... G01N 1/10
[52] U.S. Cl. ............................................... 73/422 GC
[58] Field of Search ....................... 73/422 GC, 423 A; 422/64, 65, 68

[56] References Cited

U.S. PATENT DOCUMENTS

| | | | |
|---|---|---|---|
| 3,545,279 | 12/1970 | Jentsch et al. | 73/422 GC |
| 4,000,654 | 1/1977 | Harris, Jr. | 73/423 A |
| 4,044,616 | 8/1977 | Harris, Sr. et al. | 73/423 A |

Primary Examiner—S. Clement Swisher
Attorney, Agent, or Firm—S. A. Giarratana; F. L. Masselle; E. T. Grimes

[57] ABSTRACT

Disclosed is a sample feeding apparatus having a housing defining first and second chambers sealed one from the other and a needle movable longitudinally with respect to the housing. The first and second chambers continuously receive carrier and purging gases respectively through suitable conduits. The needle has an opening normally in communication with the second chamber for continuously purging the needle. Upon application of a sample vessel to a member telescopically received about the housing, the needle is displaced through a seal into the first chamber. Carrier gas is thus provided through the needle into the head space of a sample vessel and the sample will flow to the injection block of a gas chromatograph in response to pressure compensation between the injection block and head space. Upon withdrawal of the sample vessel from below the sampling apparatus, the needle is spring returned to its initial position preventing carrier gas from flowing from the first chamber through the needle.

10 Claims, 3 Drawing Figures

SAMPLING APPARATUS FOR CHROMATOGRAPHIC INSTRUMENTS

BACKGROUND OF THE INVENTION

The present invention relates to sampling apparatus for use in gas chromatographic instruments operating in accordance with the head space method and particularly relates to a sampling apparatus and system for feeding a carrier gas into a sample vessel closed by a self-sealing diaphragm, removing a gas sample from the sample vessel, and purging the gas line of the sampling device without the necessity to supply carrier gas continuously through the apparatus.

Gas chromatographic vapor space analyses (head space) is a known technique particularly useful for the determination of volatile components in samples of heterogeneous composition where usual syringe injection fails. It is also useful for the analysis of liquids containing a high proportion of non-volatiles. In practicing the head space method, it will be appreciated that sample vessels closed by self-sealing diaphragms are used in connection with the instrument analyzing the sample. As known, a state of equilibrium obtains in the head space of the vessel above the sample liquid. In that state, the partial pressures of the sample components in the head space are a direct function of the composition of the sample. In a sampling device operating in accordance with the head space method, the sample is taken from this head space and supplied to the separating column of a gas chromatograph. To that end, prior sampling devices have included a hollow needle which is pushed through the self-sealing diaphragm and into the head space above the liquid in the sample vessel. The hollow needle lies in communication with the inlet of the injection block of the gas chromatograph. The injection block also communicates with a carrier gas conduit having a shut-off valve. With the shut-off valve initially open and the needle extending through the diaphragm of the sample vessel into the head space, carrier gas enters the head space whereby pressure builds up within the sample vessel. The partial pressures of the sample components in the head space, however, remain substantially unchanged. When the shut-off valve is subsequently closed, the carrier gas pressure at the injection block is reduced and pressure compensation causes a sample of the gas from the head space to flow through the needle into the injection block. After a predetermined time, the shut-off valve is again opened, whereby sample feeding is terminated. The gas sample, which has reached this injection block, however, is transported to the separating column of the gas chromatograph by the carrier gas flow.

To insure that carrier gas will not continue to flow unrestrictedly out of the needle after the needle has been withdrawn from the sample vessel, the needle has been disposed in a piston which is sealingly movable relative to a cylinder. This cylinder has a restricted outlet along its side and is closed by a self-sealing diaphragm at its end face in registry with the sample vessel. A compression spring acts between the piston and cylinder and biases the piston for movement in a direction away from the self-sealing diaphragm and in a manner to retract the hollow needle into the interior of the cylinder.

In this prior art arrangement, the hollow needle is stationary and communicates continuously with the injection block and the carrier gas conduit. In use, the cylinder is guided for longitudinal movement relative to the stationary hollow needle. The sample vessel is placed with its self-sealing diaphragm in engagement with the end face of the cylinder and is shifted upwardly, whereby the cylinder is pushed back about the piston and the hollow needle enters the sample vessel through the self-sealing diaphragm. In the rest position of this apparatus, a flushing or purging stream of gas flows continuously through the hollow needle, the intensity of the stream being determined by the restricted outlet from the cylinder. This purging stream insures that no vapors are carried in the hollow needle from one sample to the next sample. The foregoing arrangement is disclosed in U.S. Pat. No. 3,545,279 issued Dec. 8, 1970 and which Patent is of common assignee herewith.

SUMMARY OF THE PRESENT INVENTION

Accordingly, it is a primary object of the present invention to provide a novel and improved sample feeding apparatus and system for use in gas chromatographic instruments wherein the sample can be taken from the sample vessel without substantial loss of carrier gas.

It is another object of the present invention to provide a novel and improved sample feeding apparatus and system for use in gas chromatographic instruments and which automatically prevents communication of the carrier gas to the atmosphere once the sample vessel has been withdrawn from the sampling apparatus.

It is a still further object of the present invention to provide a novel and improved sample feeding apparatus and system for use with gas chromatographic instruments which is simple and ecomonical in construction and useful for repeated sampling.

Additional objects and advantages of the invention will be set forth in part in the description which follows and in part will be obvious from the description, or may be learned by practice of the invention. The objects and advantages of the invention may be realized and attained by means of the instrumentalities and combinations particularly pointed out in the appended claims.

To achieve the foregoing objects and in accordance with the purpose of the invention, as embodied and broadly described herein, a sample feeding apparatus in accordance with the present invention comprises a housing defining a first chamber having an inlet in communication with a source of carrier gas for conveying carrier gas into the first chamber, the housing defining a second chamber having an inlet in communication with a source of purging gas for conveying purging gas into the second chamber, means for sealing the first chamber and the second chamber one from the other, means carried by the housing defining a gas conduit including a needle having an opening adjacent one end in communication with the gas conduit, the conduit means being movable between first and second positions relative to the housing and having a gas port providing for communication between the second chamber and the gas conduit for flowing purging gas from the second chamber through the port, the gas conduit and the opening when the conduit means lies in its first position, and means for biasing the conduit means for movement into the first position, the conduit means being movable into the second position against the bias of the biasing means to locate the port in the first chamber for conveying carrier gas from the first chamber through the port, the gas conduit and the opening into the sample vessel.

The invention consists in the novel parts, constructions, arrangements, combinations and improvements shown and described. The accompanying drawings, which are incorporated in and constitute a part of the specification, illustrate an embodiment of the present invention and together with the description, serve to explain the principles of the invention.

DESCRIPTION OF A PREFERRED EMBODIMENT OF THE INVENTION

Reference will now be made in detail to the present preferred embodiment of the invention, an example of which is illustrated in the accompanying drawings.

Figure 3:
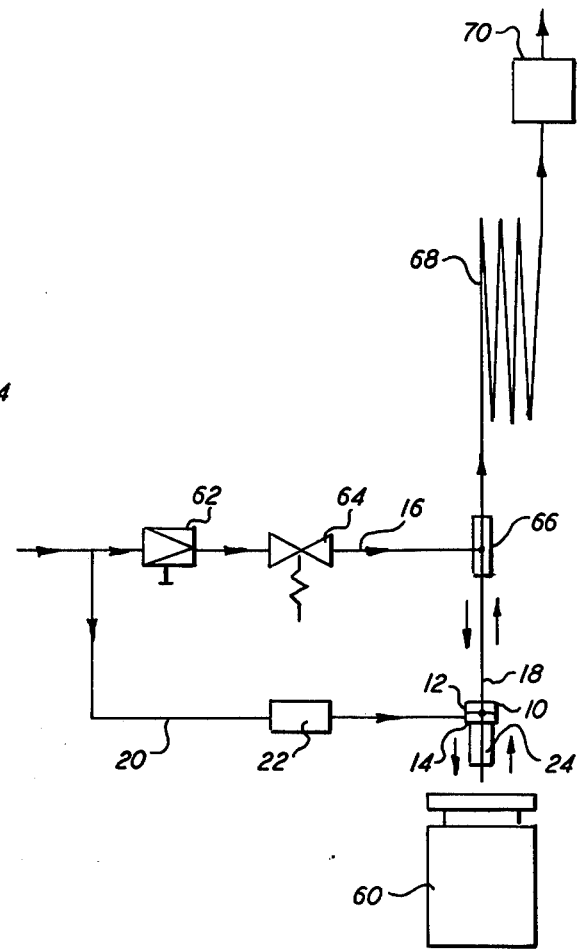
FIG. 3 is a schematic view illustrating the installation of the sample feeding apparatus of FIG. 1 in a system for use with a gas chromatograph.

Referring to the drawings, there is illustrated a sampling apparatus for feeding sample from a sample vessel 60 to the column of a gas chromatograph, not shown, and which apparatus includes a housing, generally designated 10, held stationary with respect to the gas chromatograph. Housing 10 defines an upper or first chamber 12 and a lower or second chamber 14. A branch conduit 18 of a carrier gas conduit 16 is suitably connected to housing 10 and constitutes an inlet for establishing communication via conduit 16 between first chamber 12 and a source of carrier gas, not shown, whereby carrier gas is continuously supplied first chamber 12. A branch conduit 20 is also suitably connected to housing 10 and constitutes an inlet for establishing communication between chamber 14 and a source, not shown, of purging gas whereby a stream of purging gas is continuously supplied second chamber 14. Conduit 20 constitutes a branch of carrier gas conduit 16 and contains a restrictor 22 (FIG. 3).

Means defining a gas conduit is carried by housing 10 for longitudinal movement relative thereto. Preferably, the gas conduit means includes a hollow needle 24. The first and second chambers 12 and 14, respectively, are partitioned one from the other by an annular shoulder 21, which defines an aperture 23 for receiving needle 24. Suitably secured adjacent shoulder 21 and at the lower end of a sleeve 25 carrying a tapered sealing face 27 is an annular graphite seal 26 having a complementary tapered surface 29 for sealing against face 27. Hollow needle 24 is guided for longitudinal movement through a central aperture 31 through graphite seal 26 and in sealing relation thereto. Hollow needle 24 has a lateral opening 30 adjacent its pointed lower end 28 and a lateral opening 32 adjacent its upper end and above the outlet 30, both openings 30 and 32 lying in communication with the gas conduit through needle 21.

Figure 1:
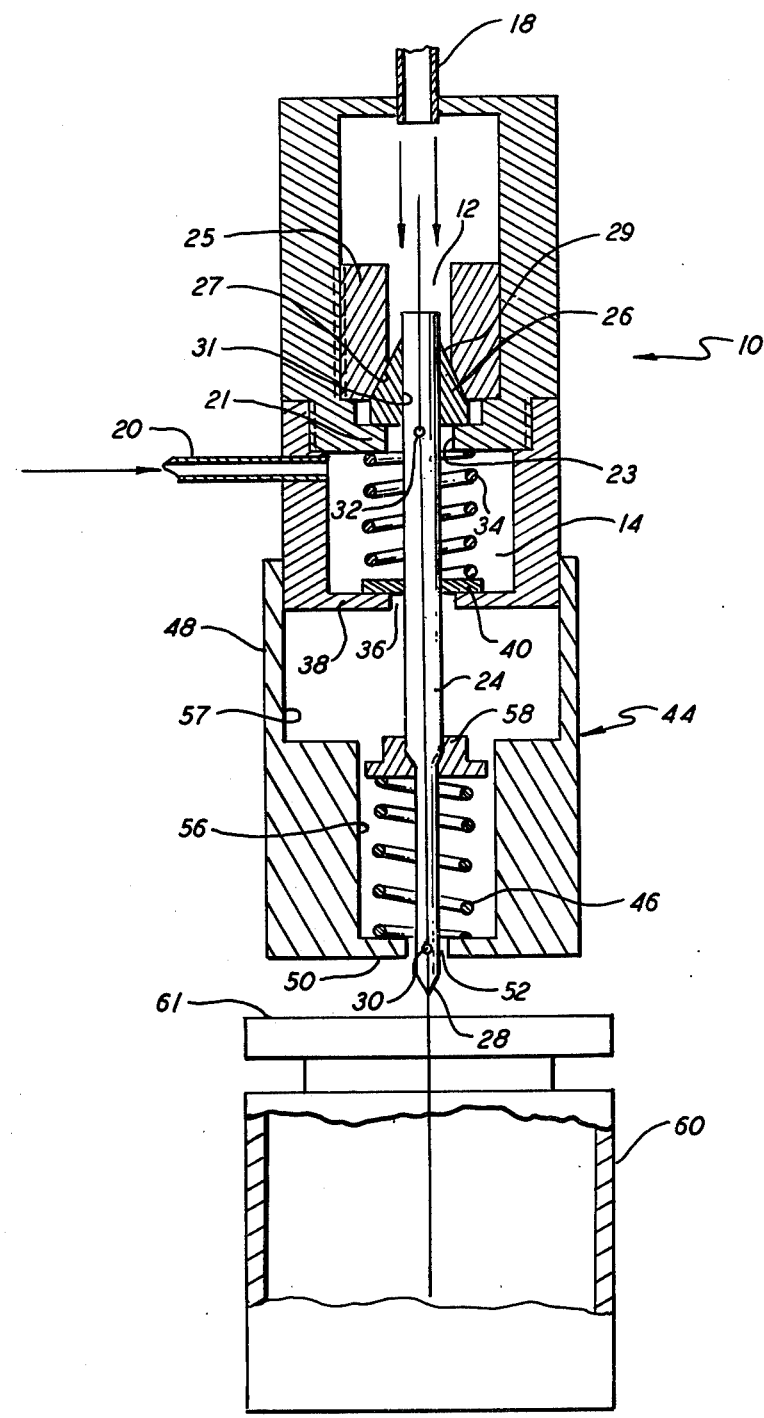
FIG. 1 is an enlarged cross-sectional view of a sample feeding apparatus constructed in accordance with the present invention and illustrated in a first or rest position.
Figure 2:
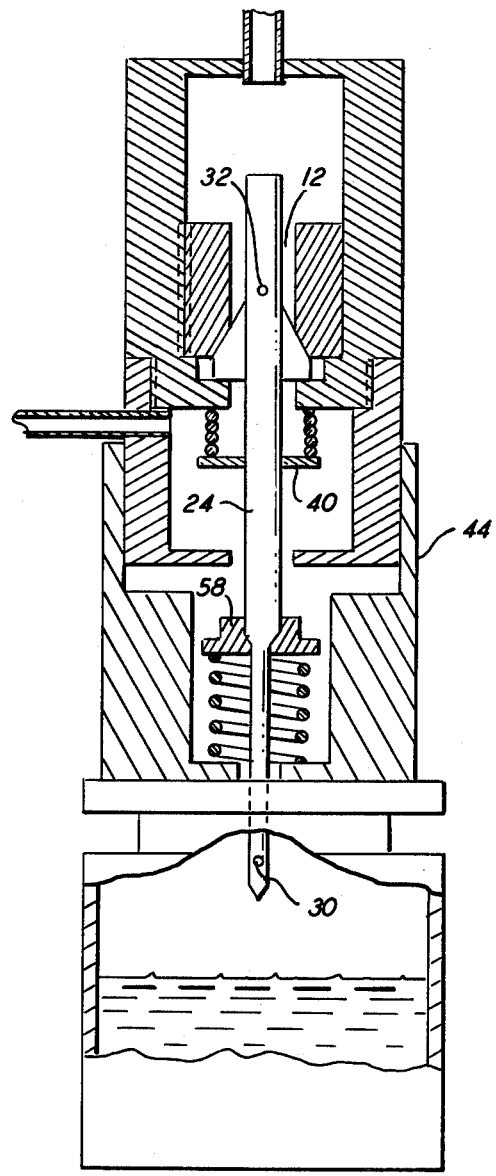
FIG. 2 is a view similar to FIG. 1 illustrating the apparatus in a second or operative position.

Needle 24 is longitudinally movable within housing 10 against the action of a return spring 34 between a lower rest or first position illustrated in FIG. 1 and an upper operative or second position illustrated in FIG. 2. In the rest position of needle 24 as illustrated in FIG. 1, opening 32 is located within second chamber 14 on the lower side of graphite seal 26 and lies in communication with the purging gas flowing into second chamber 14 through inlet 20. When moved to its operative or second position, as illustrate in FIG. 2, opening 32 is located within first chamber 12 on the other or upper side of graphite seal 26 and lies in communication with the carrier gas flowing into first chamber 12 through inlet 18. From a review of FIG. 1, it will be appreciated that hollow needle 24 passes through a central aperture 36 formed through the lower end wall 38 of housing 10 and which partially closes the lower end of second chamber 14. A spring plate 40 is suitably secured to needle 24 within second chamber 14 and engages the margin of wall 38 about central aperture 36 under the bias of return spring 34 when needle 14 lies in its rest or first position. Return spring 34 is supported at its opposite end by shoulder 21.

A generally cylindrical cup shaped member 44 is guided for longitudinal reciprocable movement on housing 10. More particularly, member 44 comprises a cylinder open at its upper end for receiving the lower end of housing 10. The upper jacket or skirt portion 48 of member 44 extends about the cylindrical outer surface of housing 10 and serves as a guide for longitudinal movement of member 44 relative to housing 10. Member 44 has a central aperture 52 through its bottom or lower end wall 50 for receiving needle 24. Member 44 also has a pair of stepped bores 56 and 57 opening through its upper end, the internal diameter of the outermost bore 57 corresponding to the outer diameter of housing 10. The smaller diameter interior bore 56 houses a compression spring 46. Spring 46 is suitably attached at one end to the bottom or lower wall 50 of member 44. A spring plate 58 is suitably secured to needle 24 at a location adjacent the juncture of bores 56 and 57 when the various parts of the apparatus lie in the position illustrated in FIG. 1 and serves as a guide for needle 24 as will become clear from the ensuing description. The other end of spring 46 bears on plate 58. As illustrated, the opening 30 of hollow needle 24 is located within the aperture 52 through the bottom or end wall 50 of member 44 when the needle 24 lies in its rest or first position. The compression spring 46 acting between member 44 and needle 24 is relaxed in the rest or first position of needle 24 and is stiffer than return spring 34.

In the illustrated rest or first position, a flushing or purging stream of gas flows continuously into second chamber 14 via inlet 20 and into opening 32 for passage through the gas conduit within hollow needle 24 and egress from opening 30. Return spring 34 retains the hollow needle in the rest position illustrated in FIG. 1.

When a sample vessel 60 with a self-sealing diaphragm 61 is urged against movable member 40 from below the apparatus, it will be appreciated that member 40 will be lifted or telescopically received about housing 10 and compression spring 46 will be compressed as illustrated in FIG. 2. Compression spring 46 acts on needle 24 so that the needle is displaced upwardly against the action of return spring 34. In this manner, inlet opening 32 is initially covered by the graphite seal 26 and is then displaced into first chamber 12. By locating opening 32 in first chamber 12, a carrier gas stream will flow from first chamber 12 through opening 32 and the gas conduit through needle 24 for egress through opening 30 and into sample vessel 60. This communication between carrier gas conduit 16 and 18 and needle 24 is not established, however, until needle 24 has pierced the self-sealing diaphragm 62 of sample vessel 60. While it is possible to displace needle 24 by the force which is required to push it though the diaphragm of the sample vessel, that force is a variable depending upon the material and thickness of the diaphragm. Consequently, member 44 and compression spring 46 are provided to ensure that diaphragm 62 is first pierced by needle 24 before opening 32 is placed in communication with the carrier gas in first chamber 12. As described hereinafter, when sufficient quantity of the sample has been drawn from the vessel and the vessel is removed from below member 44, spring 34 returns needle 24 and member 44 to their respective rest positions illustrated in FIG. 1.

The installation of the foregoing described sample feeding apparatus in a gas chromatograph is schematically illustrated in FIG. 3. Carrier gas conduit 16 contains a pressure regulator 62 and a controlled shut-off valve 64, conduit 16 opening into an injection block 66. Injection block 66 communicates with first chamber 12 of the sample feeding apparatus of the invention through branch conduit 18. Branch conduit 20 with restrictor 22 opens into second chamber 14 and branches off carrier gas in conduit 16 upstream of the pressure regulator 62. The separating column 68 of the gas chromatograph is connected to an outlet of the injection block 66 and a detector 70 is disposed at the outlet end of the column.

In operation of the system, the sample vessel 60 is placed below needle 24 and member 44 and is pressed and displaced upwardly thereagainst. Member 44 is thus telescopically received about housing 10. This action causes needle 24 to first pierce diaphragm 61 and then move in the manner described into its second position locating port 32 in first chamber 12. During this latter movement, plate 58 cooperates with bore 56 to guide and maintain needle 24 accurately centered. With shut-off valve 64 open, carrier gas will then flow through carrier gas conduit 16, branch conduit or inlet 18 into first chamber 12 and through port 32 and the gas conduit through needle 24 for egress through port 30 into sample vessel 60. After a predetermined period of time, shut-off valve 64 is closed. The reduction in pressure caused thereby at injection block 66 enables gas to flow from the head space of sample vessel 60 through opening 30, the gas conduit of needle 24, opening 32, the first chamber 12 and conduit 18 into injection block 66. This sample feeding is then terminated by once again opening shut-off valve 64 whereby the sample components, which have flowed to injection block 66, are further transported through separating column 68. After the sample vessel 60 has been withdrawn from below member 44, needle 24 returns under the bias of return spring 34 to its rest position illustrated in FIG. 1. Carrier gas is thus automatically prevented for entering needle 24 through conduit 18 because the graphite seal 26 seals between first and second chambers 12 and 14 respectively and port 32 is located in second chamber 14. Consequently, only the small flushing or purging gas stream provided second chamber 14 through conduit 20 will flow through port 32 into the gas conduit in needle 24 and outwardly thereof through port 30.

It will be apparent to those skilled in the art that various modifications and variations can be made in the sample feeding apparatus of the present invention without departing from the scope or spirit of the invention.

What is claimed is:

1. Sample feeding apparatus for use with a measuring instrument comprising:

a housing defining a first chamber having an inlet in communication with a source of carrier gas for conveying carrier gas into said first chamber, said housing defining a second chamber having an inlet in communication with a source of purging gas for conveying purging gas into said second chamber, means for sealing said first chamber and said second chamber one from the other, means carried by said housing defining a gas conduit including a needle having an opening adjacent one end in communication with said gas conduit, said conduit means being movable between first and second positions relative to said housing and having a gas port providing for communication between said second chamber and said gas conduit for flowing purging gas from said second chamber through said port, said gas conduit and said opening when said conduit means lies in its first position, and means for biasing said conduit means for movement into said first position, said conduit means being movable into said second position against the bias of said biasing means to locate said port in said first chamber for conveying carrier gas from said first chamber through said port, said gas conduit and said opening into the sample vessel.

2. Apparatus according to claim 1 wherein said needle carries said gas port, said port being located on one side of said sealing means in communication with said second chamber when said conduit means lies in said first position and being located on the opposite side of said sealing means in communication with said first chamber when said conduit means lies in said second position.

3. Apparatus according to claim 1 including a member carried by said housing and movable between a first position extended from said housing and a second position closely adjacent said housing, and means coupled between said member and said gas conduit means for moving said gas conduit means toward said housing in response to movement of said member from said first position toward said second position.

4. Apparatus according to claim 3 wherein said coupling means includes a spring for biasing said member for movement relative to said housing toward its first extended position.

5. Apparatus according to claim 3 wherein said member is generally cup shaped having an open end for slidably receiving an end of said housing, said member having an aperture at its opposite end for receiving said needle.

6. Apparatus according to claim 3 wherein said member is generally cylindrical and has stepped bores opening through one end thereof, the outermost stepped bore slidably receiving an end of said housing, said coupling means including a spring receivable in the smaller diameter bore of said member, and an abutment carried by said needle, said spring engaging said abutment and said member at its respective opposite ends, and biasing said member for returning movement from its second position to the first position, said member having an aperture at its opposite end for receiving said needle.

7. Apparatus according to claim 6 wherein said abutment is receivable in said smaller diameter bore upon movement upon said member toward its second position to serve as a guide and support for said needle when said member and said needle are moved toward their respective second positions.

8. In a gas chromatographic system having an injection block for a gas chromatograph, means for conveying a carrier gas into and through said injection block, a valve carried by said conveying means, and a conduit for carrying purging gas, sample feeding apparatus for use with the gas chromatographic system including;

a housing defining a first chamber having an inlet in communication with the carrier gas conveying means for conveying carrier gas into said first chamber when the valve is open, said housing defining a second chamber having an inlet in communication with said purging gas conduit for conveying purging gas into said second chamber, means for sealing said first chamber and said second chamber one from the other, means carried by said housing defining a gas conduit including a needle having an opening adjacent one end in communication with said gas conduit, said conduit means being movable between first and second positions relative to said housing and having a gas port providing for communication between said second chamber and said gas conduit for flowing purging gas from said second chamber through said port, said gas conduit and said opening when said conduit means lies in its first position, and means for releasably retaining said conduit means in said first position, said conduit means being movable into said second position to locate said port in said first chamber for conveying carrier gas from said first chamber through said port, said gas conduit and said opening into the sample vessel when the valve is open and for conveying sample from the sample vessel through said opening, said gas conduit, said port, said first chamber and the gas conveying means into the injection block when the valve is closed.

9. A gas chromatographic system according to claim 8 wherein said needle carries said gas port, said port being located on one side of said sealing means in communication with said second chamber when said conduit means lies in said first position and being located on the opposite side of said sealing means in communication with said first chamber when said conduit means lies in said second position, a member carried by said housing and movable between a first position extended from said housing and a second position closely adjacent said housing, and means coupled between said member and said gas conduit means for moving said gas conduit means toward said housing in response to movement of said member from said first position toward said second position.

10. A gas chromatographic system according to claim 3 wherein said coupling means includes a spring for biasing said member for movement relative to said housing toward its first extended position.

* * * * *